United States Patent
Burns et al.

(10) Patent No.: US 6,511,449 B2
(45) Date of Patent: Jan. 28, 2003

(54) INFLATABLE BRACE SYSTEM

(75) Inventors: Michael Burns, Laconia, NH (US);
Paul Burns, Warwick, RI (US); Gary Burns, Warwick, RI (US)

(73) Assignee: Phoenix International, Laconia, NH (US)

(*) Notice: Subject to any disclaimer, the term of this patent is extended or adjusted under 35 U.S.C. 154(b) by 0 days.

(21) Appl. No.: 09/876,427

(22) Filed: Jun. 7, 2001

(65) Prior Publication Data

US 2002/0193717 A1 Dec. 19, 2002

(51) Int. Cl.[7] .................................................. A61F 5/00
(52) U.S. Cl. ....................... 602/13; 602/27; 128/DIG. 20
(58) Field of Search ................................ 602/12, 13, 6, 602/9, 23, 27, 65; 128/DIG. 20

(56) References Cited

U.S. PATENT DOCUMENTS

| | | | |
|---|---|---|---|
| 4,977,891 A | * 12/1990 | Grim | 602/27 |
| 5,125,400 A | * 6/1992 | Johnson, Jr. | 602/13 |
| 5,348,530 A | * 9/1994 | Grim et al. | 602/13 |
| 5,641,322 A | * 6/1997 | Silver et al. | 602/13 |
| 5,643,185 A | * 7/1997 | Watson et al. | 602/26 |
| 5,792,084 A | * 8/1998 | Wilson et al. | 602/13 |

* cited by examiner

Primary Examiner—Michael A. Brown
Assistant Examiner—Quang D Thanh
(74) Attorney, Agent, or Firm—Michael J. Persson; Lawson, Philpot & Persson, P.C.

(57) ABSTRACT

An inflatable cast system for immobilizing a lower extremity of a human. The system includes a pair of outer shell members shaped to conform to the lateral and medial sides of the lower extremity, respectively. A base member is fastened to the shell members to form a substantially U-shaped stirrup member. The upstanding sidewalls of the shell members are maintained in position relative to the lower extremity by a plurality of elongated, circumferentially extending, longitudinally spaced, flexible fastening straps. A pair of inflatable air bags are attached to inside surfaces of the shell members. The air bags include at least one chamber and a valve that is sealed along one edge of the air bag and is adapted to allow the chamber to be automatically sealed once the brace is attached to the extremity of the user. A unidirectional air pump is provided to allow the chamber of the air bag to be selectively inflated and deflated. The air pump includes in inflation orifice and a deflation orifice that are dimensioned to be inserted within a top portion of the valve. A bulb portion of the pump causes air to be drawn in through the deflation orifice and out through the inflation orifice when squeezed.

16 Claims, 6 Drawing Sheets

INFLATABLE BRACE SYSTEM

FIELD OF THE INVENTION

The present invention relates to the field of brace systems and, in particular, to an inflatable ankle brace system that is easily and controllably inflated and deflated.

BACKGROUND OF THE INVENTION

Inflatable ankle braces have been used for many years in the management of certain injuries to the lower extremities. These braces, commonly referred to as air casts, are typically utilized after immobilization of the extremity by a molded plastic or resin cast has stabilized the injury to a point where some weight may be placed upon the extremity.

Air casts typically include substantially rigid right and left outer shell members that are joined at the bottom by a flexible stirrup and shaped to fit a patient's ankle. The inside surfaces of these shell members are typically padded in selected areas and include some means for attaching an inner air cell or bladder. These air cells or bladders may include one or more compartments that may be inflated by the patient, or may be factory inflated. In addition, some such air casts include one or more compartments filled with a cushioning gel and/or multiple layers of open cell foam to provide additional padding.

Inflatable air casts have traditionally been inflated via a manual inflation tube that extends into the air bladder and is pressurized by the patient in a manner similar to the inflation of a balloon. Once pressurized, the tube is removed and the end sealed to prevent the escape of air. This inflation system is relatively inexpensive and provides for adequate inflation in many instances. However, it is not without its drawbacks. For example, patients having reduced lung capacity, due to age, respiratory disease or the like, may not be able to provide sufficient pressure into the tube to adequately inflate the bladder. In addition, air may escape during withdrawal of the tube, further reducing the pressure within the bladder. Also, the use of a tube does not allow for selective addition removal of air to reduce pressure in the event that the bladder has been under-pressurized or over-pressurized. Finally, the tubes used to inflate the bladders in these systems are not readily adapted to being transported in a patient's pocket and, therefore, are not likely to be taken with the patient outside of the patient's home.

Therefore, there is a need for an inflatable cast system that includes a means of inflation and deflation that allows people with reduced respiratory capacity to adequately inflate the air bladder, allows the bladder to be selectively inflated and deflated, and is easily transported with the patient.

SUMMARY OF THE INVENTION

The present invention is an inflatable brace system for immobilizing a lower extremity of a human. In its most basic form, the system includes a pair of outer shell members shaped to conform to the lateral and medial sides of the lower extremity, respectively. A base member having a pair of oppositely extending hinge portions are inserted through transverse slots proximal to the lower edges of shell members and are fastened to the shell members. Thus attached, the base member forms a substantially U-shaped stirrup member adapted to be fitted about the lower extremity with the heel of the foot resting upon the base member and the opposed shell members forming a pair of upwardly extending sidewall portions adapted to be flexed into confronting engagement with corresponding opposed side portions of the lower extremity. The upstanding sidewalls of the shell members are maintained in position relative to the lower extremity by a plurality of elongated, circumferentially extending, longitudinally spaced, flexible fastening straps. A pair of inflatable air bags are attached to inside surfaces of the shell members. The air bags include at least one chamber and a valve that is sealed along one edge of the air bag. The valve is adapted to allow the chamber to be automatically sealed once the brace is attached to the extremity of the user. A unidirectional air pump is provided to allow the chamber of the air bag to be selectively inflated and deflated. The air pump includes an inflation orifice and a deflation orifice that are each dimensioned to be inserted within a top portion of the valve. A bulb portion of the pump causes air to be drawn in through the deflation orifice and out through the inflation orifice when squeezed.

In operation, the inflation orifice of the pump is inserted within the top portion of the valve and the bulb is squeeze in order to inflate the air bag before the patient attaches the brace about his lower extremity. The user will then adjust the pressure in the air bag by inserting the inflation orifice or deflation orifice of the pump into the top portion of the valve and squeezing the bulb until the desired pressure is achieved.

In the preferred embodiment of the system, a cushioning member is inserted with in the chamber prior to sealing. The preferred cushioning member is a sheet of open cell foam that extends substantially across the entire interior of the chamber. However, in other embodiments, the cushioning member is a gel pack that is placed in a lower portion of the chamber. In still other embodiments, the cushioning member includes a combination of a gel pack and an open cell foam that are selectively disposed within the chamber.

Therefore, it is an aspect of the invention to provide an inflatable cast system that includes a means of inflation and deflation that allows people with reduced respiratory capacity to adequately inflate the air bladder.

It is a further aspect of the invention to provide an inflatable cast system that includes a means of inflation and deflation that allows the bladder to be selectively inflated. and deflated.

It is a still further aspect of the invention to provide an inflatable cast system that includes a means of inflation and deflation that is relatively inexpensive.

It is a still further aspect of the invention to provide an inflatable cast system that includes a means of inflation and deflation that is easily transported by a patient.

These aspects of the invention are not meant to be exclusive and other features, aspects, and advantages of the present invention will be readily apparent to those of ordinary skill in the art when read in conjunction with the following description, appended claims and accompanying drawings.

DETAILED DESCRIPTION OF THE INVENTION

Figure 1:
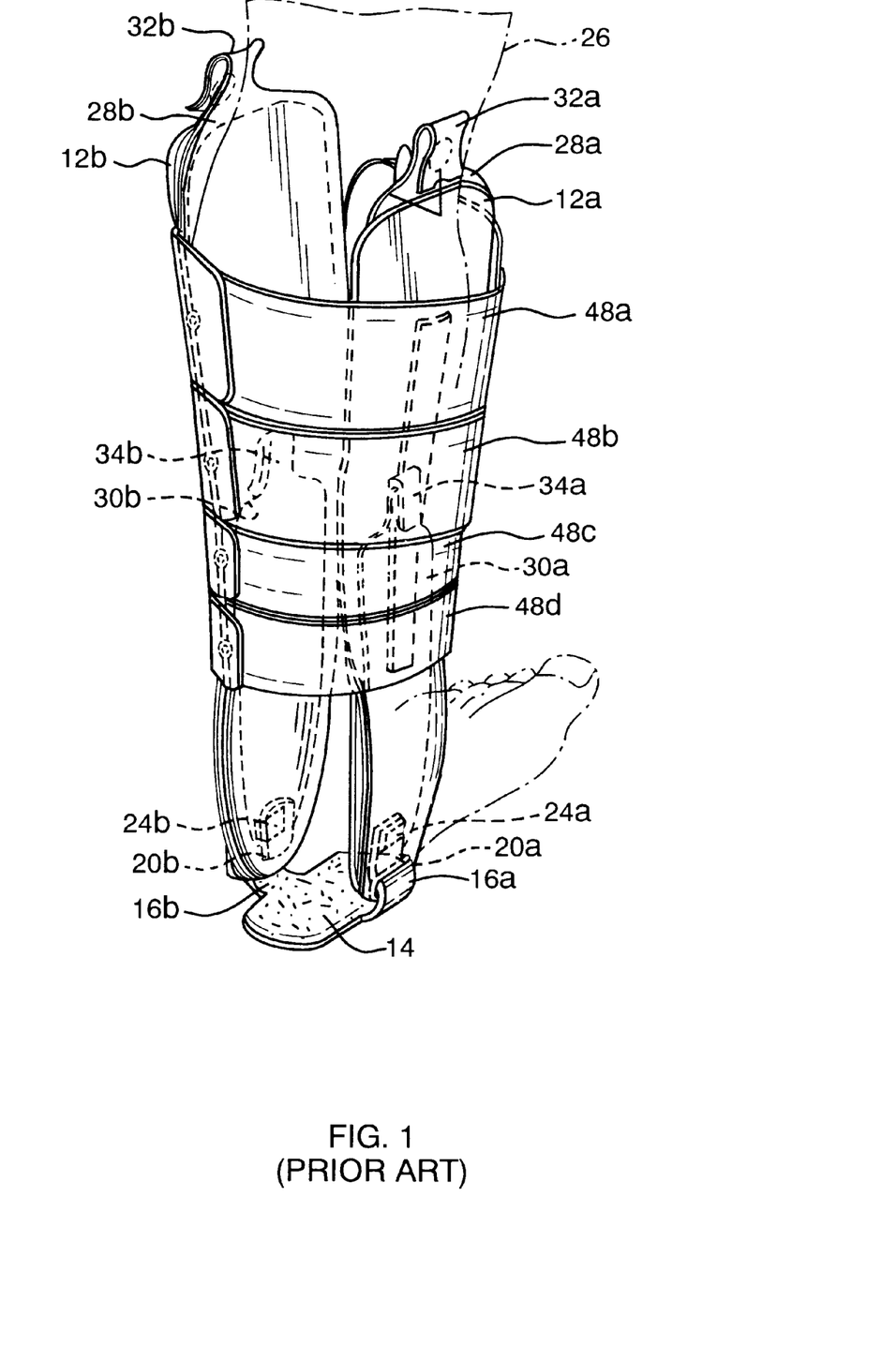
FIG. 1 is a is a schematic, perspective view of a prior art inflatable cast assembled and fitted about an imaginary lower extremity of a human.

Referring first to FIG. 1, a prior art inflatable brace 10 is shown. Inflatable brace 10 is adapted to be fitted about the lower extremity of a human and comprises a pair of outer shell members 12a, 12b, preferably of a stiff, durable, molded plastic material and generally shaped to conform to the lateral and medial sides of the lower extremity, respectively, and a base member 14 having a pair of oppositely extending, hinge portions 16a, 16b. The base member 14 and hinge portions 16a, 16b are formed from a common piece of flexible woven nylon material cut to size and shaped substantially as shown, and have bonded thereto a layer of fastener material such as that commonly sold under the VELCRO trademark. The distal ends of hinge portions 16a, 16b are adapted to be inserted through transverse slots 20a, 20b proximal to the lower edges of shell members 12a, 12b and thereupon be fastened to a pair of mating VELCRO fastener patch elements 24a, 24b in slightly spaced relation above slots 20a, 20b by means of a suitable adhesive. When the shell members 12a, 12b and the base portion 14 are so assembled, there is formed a U-shaped stirrup member adapted to be fitted about the lower extremity with the heel of the foot resting upon the base member and the opposed shell members forming a pair of upwardly extending sidewall portions adapted to be flexed or displaced via hinge portions 16a, 16b into confronting engagement with corresponding opposed side portions of the lower extremity 26. As shown in FIG. 1, a pair of separate, differently size, flexible, inflatable air bags 28a, 28b and 30a, 30b are disposed in a juxtaposed, overlapping manner on the inwardly facing, confronting surfaces of sidewall members 12a, 12b. Thus, sidewall member 12a has associated therewith a first inflatable air bag 28a which extends substantially coextensively with respect to the inner surface of sidewall member 12a, and a second inflatable air bag 30a which extends substantially coextensively with respect to approximately the bottom half of both the inner surface and the corresponding confronting surface of air bag 28a, i.e. air bag 30a is about one half as large as air bag 28a, is disposed between sidewall member 12a and air bag 28a, and is substantially coextensively aligned with approximately the bottom half portion of air bag 28a. Likewise, sidewall member 12b has associated therewith a first inflatable air bag 28b and a second inflatable air bag 30b that are disposed in substantially the same manner as the air bags 28a, 30a described above. However, it is also common to employ a single air bag in place of the dual air bag arrangement described herein.

Each of the inflatable, flexible liners or air bags 28a, 28b, 30a, 30b comprises a pair of similarly sized, opposed, thin sheets of pliable material, such as vinyl plastic, that are bonded together along their confronting peripheries using known joining techniques such as heat or electronic bonding. Each such air bag 28a, 28b, 30a, 30b further includes an integral valve 32a, 32b, 34a, 34b extending upwardly therefrom and having a normally sealed throat through which a flexible plastic tube (not shown) may be inserted to facilitate selective inflation or pressurization of each air bag via mouth entubation. Each valve may carry exteriorly a pair of spaced, cooperating VELCRO fastener elements to enable the valve to be folded down upon itself and fastened in place thereby presenting a neater appearance and helping to avoid leakage of air through the throat of each valve. Finally, each air bag is preferably preinflated by having inserted therein during fabrication a filler member or pad of compressible, resilient, porous material, preferably open or closed cell urethane foam, that is shaped and sized to substantially completely fill the interior volume of each air bag, respectively.

The assembled leg brace 10 is fitted about the lower extremity 26 of a human with the sidewall members 12a, 12b flexed or displaced toward and into engagement with corresponding confronting medial and lateral portions of the foot, ankle and lower leg. By such arrangement, air bags 28a, 30a, 28b, 30b will be compressed sufficiently to provide a pressurized air cushion or envelope circumferentially engaging the lower extremity and filling the voids between the inner surfaces of the upstanding sidewall members and the irregular contours of the lower extremity.

In order to maintain this desired relationship, and the appropriate magnitude of pressurization inside the air bags, the upstanding sidewalls are maintained in position relative to the lower extremity by a plurality of elongated, circumferentially extending, longitudinally spaced, flexible fastening straps 48a–d. Each strap 48a–d is fabricated of the same well known woven nylon material as base member 14 and therefore includes a layer of VELCRO fastening material on the underside thereof. Each strap is securely affixed to, or terminates in, a respective VELCRO fastener patch element which, in turn, is securely attached to the outer surface of shell member 12b, preferably by means of a suitable adhesive, with the patch elements being adapted to securely mate with the VELCRO fastening material on the underside of each strap member. Thus, one end of each strap member 48a–d has its corresponding patch element anchored to shell member 12a thereby permitting the underside of the other or distal free end of each strap member to be securely fastened to such corresponding fastener patch element after the strap members are circumferentially drawn and tensioned snugly about the exterior of the shell members.

Figure 2:
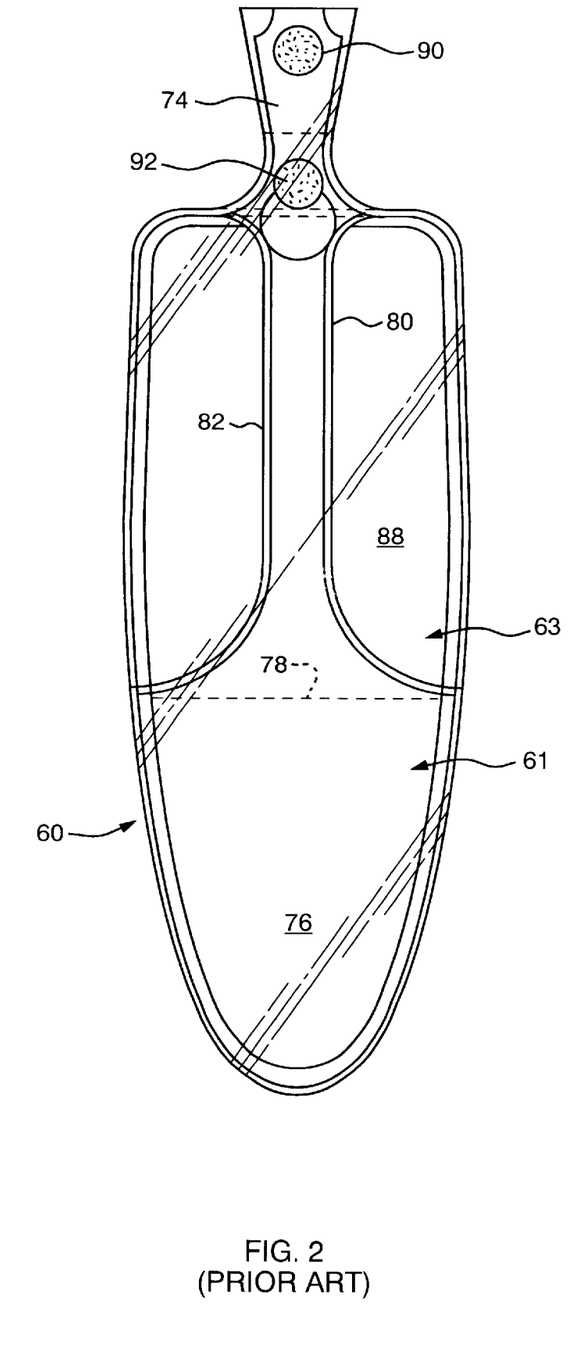
FIG. 2 is a view in elevation of a prior art air bag.

Referring now to FIG. 2, another prior art air bag 60 is shown. Air bag 60 is made by joining three relatively thin, sheets or plies and together along their common peripheral extents to form a pair of pressurizable chambers interiorly. Each ply includes an integral extension and end flap which form a self-sealing valve member 74 when the plies are sealed. This valve member 74 is adapted to seal any air in a first chamber formed interiorly of the joined plies, thus preventing loss of internal pressurization, and may be selectively be opened as by inserting a suitably sized plastic tube inserted between the confronting flaps to admit or exhaust air from the first chamber 61.

The first chamber 61 in unitary member 60 is formed and pre-inflated by positioning a first filler member or pad 76 of porous, compressible material between the plies before the latter are bonded together. The first filler member 76 has a shape and size conforming substantially to the bottom portion and terminates in a relatively straight, horizontally extending upper boundary 78 defining the upper extremity of the first chamber 61. The plies are also bonded together locally along a pair of seams 80, 82 which extend inwardly from their intersection with the opposed edges of the plies immediately above upper boundary 78 of first filler member 76. Seams 80, 82 then extend arcuately upwardly substantially as shown in spaced relation to one another until they arcuately intersect the upper edges of plies on either side of the base portion defining integral valve extension 74. By this arrangement, a longitudinally extending thru-passage 84 is formed between the plies connecting the valve 74 with the upper portion of the first chamber 61. The second chamber 63 in unitary member 60 is formed coextensively with substantially the entire extent of the plies and, as is the case with the first chamber 61, preferably is pre-inflated. This is accomplished by positioning a second filler member 88, of the same material as filler member 76, and then bonding the plies together along their common peripheral extents using known heat or electronic sealing methods.

The resulting unitary member 60 comprises a pair of pressurizable chambers divided by a common wall with the first chamber 61 extending coextensively with respect to substantially the entire member, and the second chamber 63 extending only partially coextensively with respect to the member 60 and the first chamber 61.

The unitary member 60 also includes valve means 74 for selectively inflating only the other chamber with the valve means being comprised in part by said common wall. Finally, a pair of VELCRO mating fasteners 90, 92 may be affixed to the valve exterior 74 so that the valve 74 may be folded upon itself and fastened in place.

Figure 3:
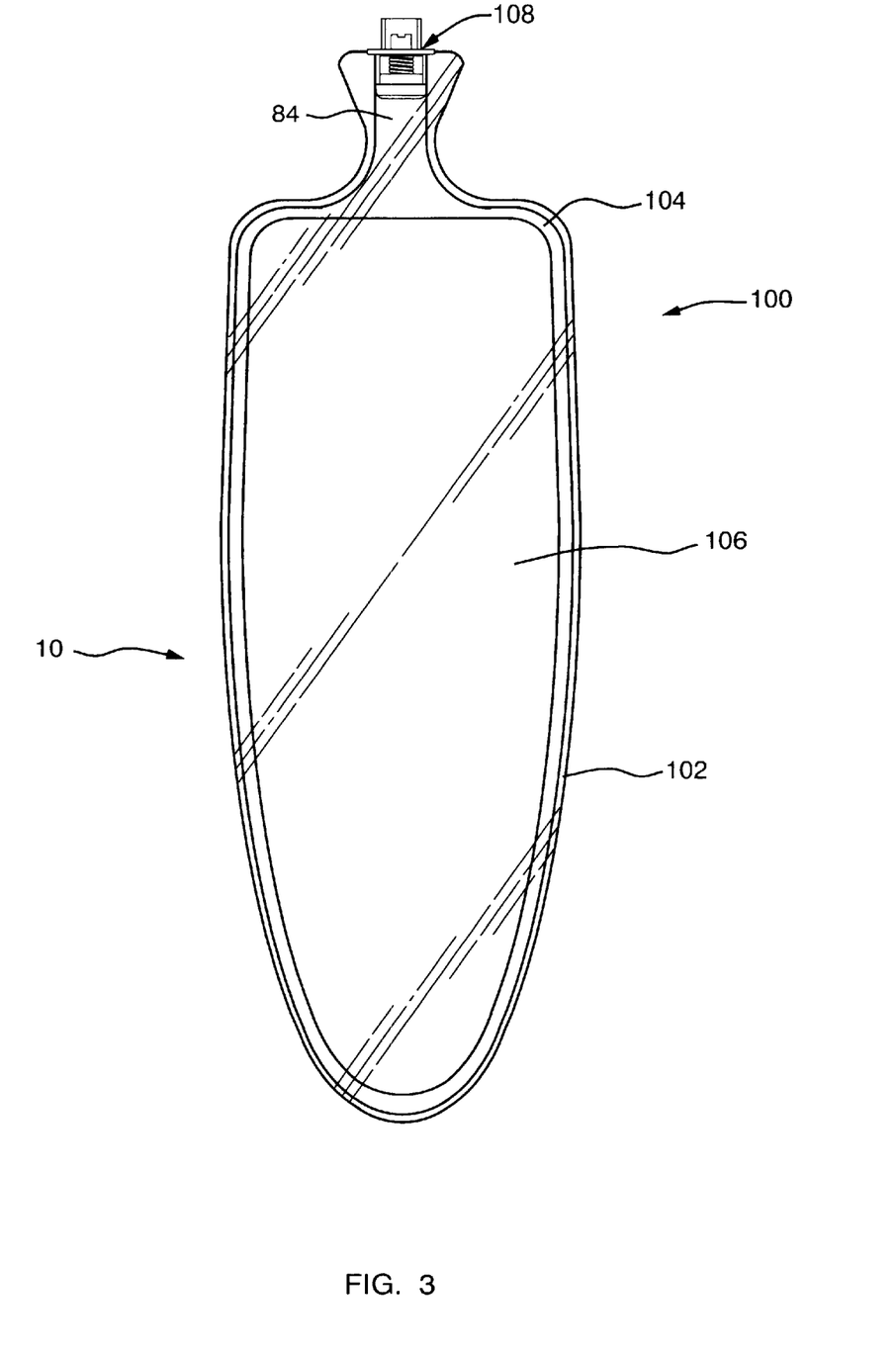
FIG. 3 is a view in elevation of the air bag of the preferred embodiment of the system of the present invention.

Referring now to FIG. 3, the air bag 100 of the preferred system of the present invention is shown. The preferred air bag 100 is manufactured from two plies of a substantially flexible material, such as vinyl plastic, that are sealed about their periphery 102 in a manner similar to the prior art method described above. The resulting air bag 100 includes a single inner chamber 104 within which is disposed a cushioning material 106. Cushioning material 106 is preferably a single sheet of open cell urethane foam, such as the foam described above. However, it is recognized that gel pouches, cotton batting or other art recognized cushioning materials may be utilized to achieve similar results.

Figure 4:
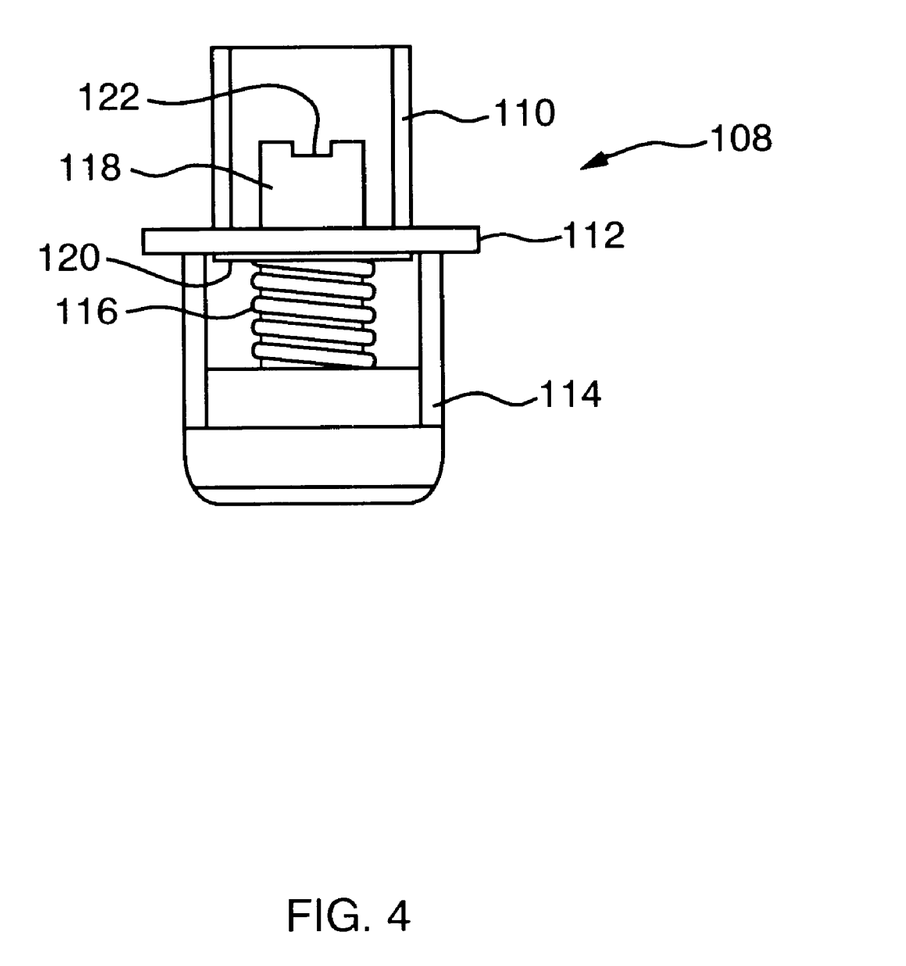
FIG. 4 is a cut away side view of the valve of the preferred embodiment of the system of the present invention.

Referring now to FIGS. 3 and 4, air bag 100 includes a spring loaded valve 108 that is sealed between the plies in such a manner as to prevent air leakage when the air bag 100 is inflated. Valve 108 includes a top portion 110 that extends above the plies of the air bag 100, a shoulder portion 112 that is dimensioned to sit atop the plies and prevent the valve from being pushed in to the air bag 100, and a lower portion 114 that is dimensioned to be heat sealed between the plies of the air bag 100. However, it is recognized that the valve 108 may be attached at different locations and using different art recognized means. A spring 116 is mounted within the lower portion 114 and acts to bias a valve pin 118 upward to maintain the valve 108 in a closed position. The valve pin 118 includes a sealing ring 120 along its bottom surface for sealing off the valve when in the closed position, and a notch 122 along its top surface for allowing air to flow into the air bag 100 when the valve pin 118 is depressed.

Figure 5:
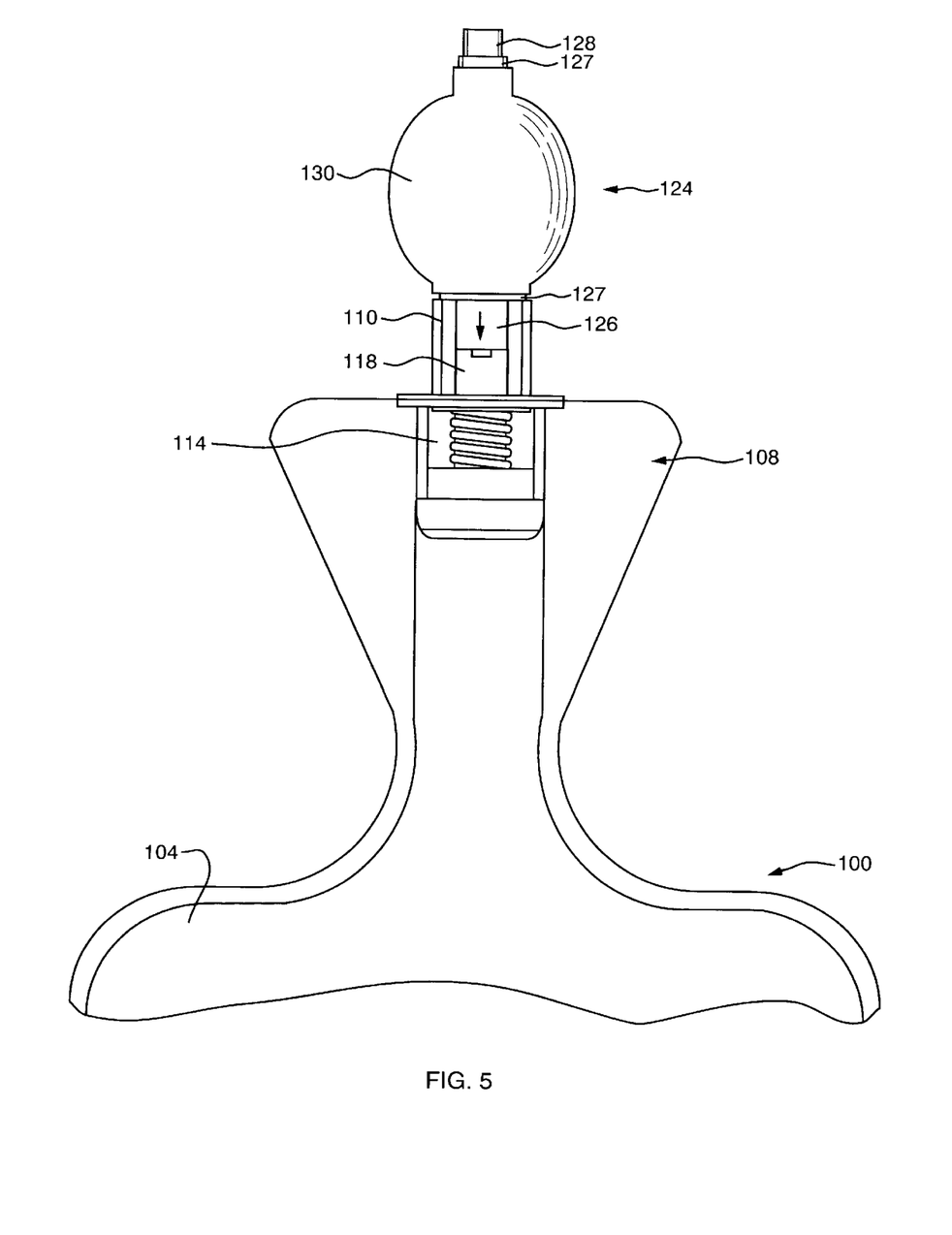
FIG. 5 is a front view of the valve and unidirectional pump of the preferred embodiment of the system of the present invention.

As shown in FIG. 5, the air bag 100 is inflated by inserted an inflation orifice 126 of a bulb type pump 124 into the top portion 110 of the valve 108. During inflation, the inflation orifice 126 depresses the valve pin 118 to allow air to create a fluid path between top portion 110 and the lower portion 114. The shoulder portion 127 of the pump 124 is then brought into contact with the rim of the top portion 110 such that air is prevented from escaping. Air is then pumped through the inflation orifice 126 into the chamber 104 of the air bag 100.

In these embodiments, the pump 124 is a dual bladder pump having an inflation orifice 126 and a deflation orifice 128. In such a pump 124, manually squeezing of the bulb 130 of the pump causes air to be drawn into the pump 124 through the deflation orifice 128 and to be exhausted through the inflation orifice 126. Because of the unidirectional nature of the airflow through such a pump 124, this pump 124 is readily adapted to controllably deflate the air bag 100 by simply inserting the deflation orifice 128 into the top portion 110 of the valve 108 and squeezing the bulb in a similar manner. In the system of the present invention, a pair of air bags 100 are utilized in place of the air bags 28a, 28b, 30a, 30b of the prior art brace 10 described with reference to FIG. 1, and also includes the pump 124 described with reference to FIG. 5. In operation, the pump 124 is used to inflate the air bag 100 before the patient attaches the brace about his lower extremity. The user will then adjust the pressure in the air bag 100 be inserting the inflation orifice 126 or deflation orifice 128 of the pump into the top portion 100 of the valve 108 and squeezing the bulb 130 until the desired pressure is acheived.

Figure 6:
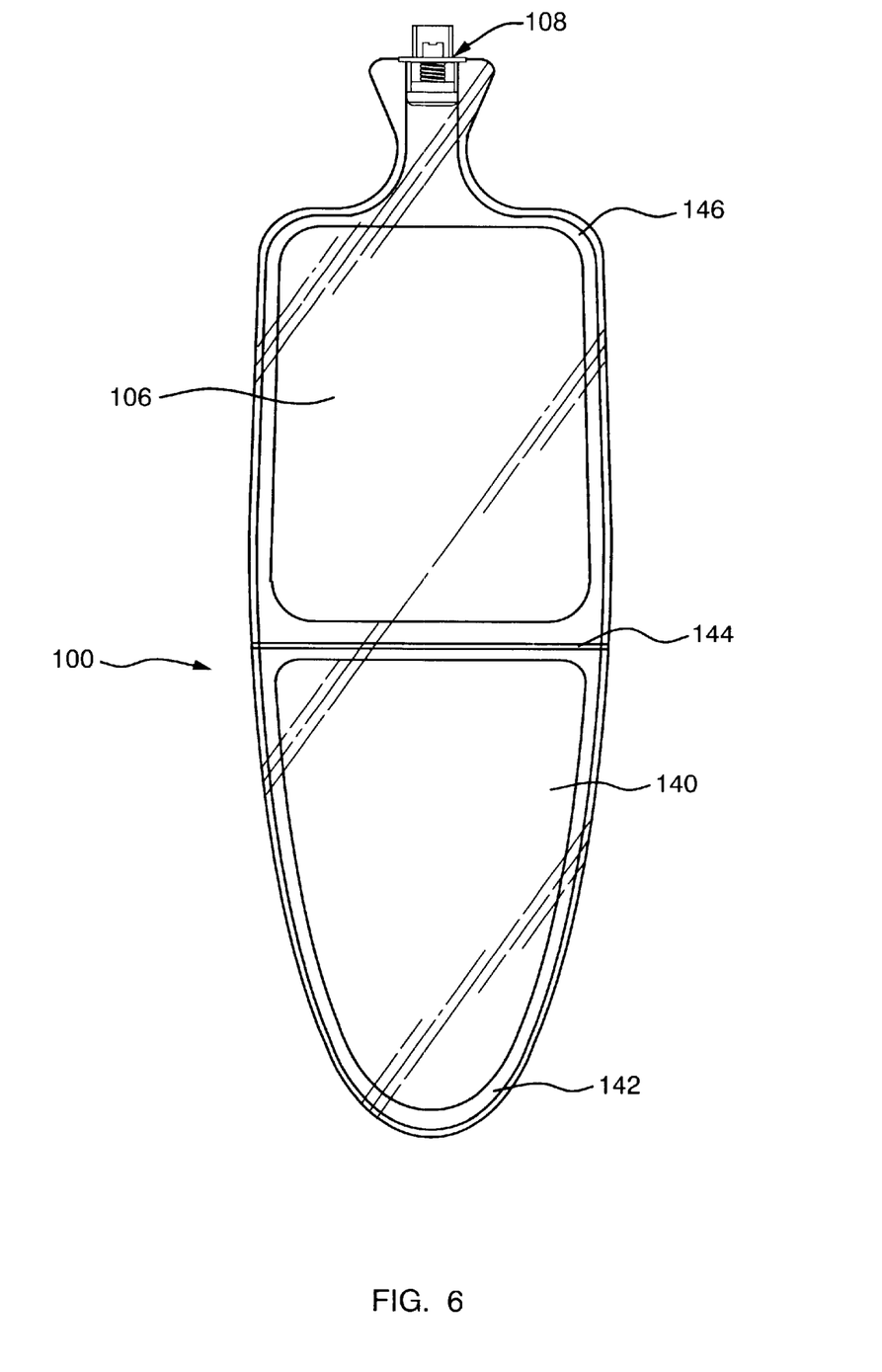
FIG. 6 is a view in elevation of an air bag utilized in an alternative embodiment of the system of the present invention.

Referring now to FIG. 6, an alternative embodiment of the air bag 100 of the system of the present invention is shown. In this embodiment, a gel pack 140 is disposed within a lower chamber 142 of the air bag 100 and is sealed in place along a seam 144 created between the lower chamber 142 and the upper chamber 146 of the air bag 100. The upper chamber 146 of the air bag 100 is similar to the corresponding chamber of the air bag 100 described with reference to FIG. 3 and includes the same valve 108 sealed along its top edge. In this embodiment, the upper chamber 146 of the air bag 100 includes a cushioning member 106 and is inflated in the same manner as describe above, while the flow of air being prevented from entering the lower portion 142 by seam 144.

In other embodiments of the system of the present invention, the air bag 100 is similar to the air bag 60 described with reference to FIG. 2, except a gel pack is used in place of the pad 76 and the valve 108 is used in place of the valve 74. In still other embodiments, the air bag 100 includes all of the elements of the air bag 60 of FIG. 2, except for the use of the valve 108 in place of the valve 74.

Although the present invention has been described in considerable detail with reference to certain preferred versions thereof, other versions would be readily apparent to those of ordinary skill in the art. Therefore, the spirit and scope of the claims should not be limited to the description of the preferred versions contained herein.

What is claimed is:

1. An inflatable brace system for immobilizing a lower extremity of a human, said system comprising:
   a brace comprising;
      a pair of outer shell members shaped to conform to a lateral side and a medial side of said lower extremity, said shell members each having a lower edge;
      a base member fastened to said lower edge of each shell member;
      at least one fastening strap attached to at least one of said shell member and dimensioned to maintain said shell members in position relative to said lower extremity; and
      a pair of inflatable air bags attached to inside surfaces of the shell members, each air bag having at least one peripheral edge and comprising at least one chamber and a valve that is sealed along said edge of said air bag and adapted to allow said chamber to be automatically sealed once said brace is attached to the extremity of the user; and
      a unidirectional air pump dimensioned to be attached to said valve and selectively inflate and deflate said chamber of said air bag.

2. The inflatable brace system as claimed in claim 1, wherein said lower edge of each of said shell members comprises a transverse slot disposed therethrough, and wherein said base member comprises a pair of oppositely extending hinge portions inserted through said transverse slots in said base member to form a substantially U-shaped stirrup member dimensioned to be fitted about the lower extremity with a heel of a foot resting upon said base member and said shell members forming a pair of upwardly extending sidewall portions.

3. The inflatable brace system as claimed in claim 1 wherein said at least one fastening strap comprises a plurality of elongated fastening straps dimensioned to circumferentially extend longitudinally about said shell members.

4. The inflatable brace system as claimed in claim 1 wherein said air pump comprises an inflation orifice and a deflation orifice.

5. The inflatable brace system as claimed in claim 4 wherein said air pump comprises a bulb portion dimensioned to cause air to be drawn in through the deflation orifice and out through the inflation orifice when squeezed by a user.

6. The inflatable brace system as claimed in claim 5 wherein said valve comprises a valve pin and wherein said inflation orifice is dimensioned to depress said valve pin to allow air to enter said chamber.

7. The inflatable brace system as claimed in claim 6 wherein said inflation orifice and said deflation orifice of said air pump each comprise a shoulder portion and wherein said valve comprises a rim that is dimensioned to sealably contact said shoulder portion to prevent air from escaping.

8. The inflatable brace system as claimed in claim 1 wherein at least one of said air bags further comprises at least one cushioning member disposed within said chamber prior to sealing.

9. The inflatable brace system as claimed in claim 8 wherein said at least one cushioning member is at least one sheet of open cell foam.

10. The inflatable brace system as claimed in claim 8 wherein said at least one cushioning member extends substantially across an entire interior of said chamber.

11. The inflatable brace system as claimed in claim 8 wherein said at least one cushioning member is at least one gel pack.

12. The inflatable brace system as claimed in claim 8 wherein said chamber comprises an upper portion and a lower portion and wherein at least one cushioning member is disposed in said lower portion of said chamber.

13. The inflatable brace system as claimed in claim 12 wherein said at least one cushioning member is at least one sheet of open cell foam.

14. The inflatable brace system as claimed in claim 12 wherein said at least one cushioning member is at least one gel pack.

15. The inflatable brace system as claimed in claim 12 wherein said at least one cushioning member comprises a gel pack disposed in said lower portion of said chamber.

16. The inflatable brace system as claimed in claim 15 wherein said at least one cushioning member further comprises at least one sheet of open cell foam disposed in said upper portion of said chamber.

* * * * *